United States Patent
Sato et al.

(10) Patent No.: US 12,187,886 B2
(45) Date of Patent: Jan. 7, 2025

(54) HYDROGEL

(71) Applicant: SEKISUI KASEI CO., LTD., Osaka (JP)

(72) Inventors: Eisaku Sato, Osaka (JP); Takahiko Fujita, Osaka (JP)

(73) Assignee: SEKISUI KASEI CO., LTD., Osaka (JP)

( * ) Notice: Subject to any disclaimer, the term of this patent is extended or adjusted under 35 U.S.C. 154(b) by 124 days.

(21) Appl. No.: 17/042,107

(22) PCT Filed: Mar. 25, 2019

(86) PCT No.: PCT/JP2019/012413
§ 371 (c)(1),
(2) Date: Sep. 26, 2020

(87) PCT Pub. No.: WO2019/188936
PCT Pub. Date: Oct. 3, 2019

(65) Prior Publication Data
US 2021/0102059 A1 Apr. 8, 2021

(30) Foreign Application Priority Data
Mar. 30, 2018 (JP) .................................. 2018-069422

(51) Int. Cl.
| | | |
|---|---|---|
| *C08L 33/26* | (2006.01) | |
| *A61L 26/00* | (2006.01) | |
| *A61L 31/04* | (2006.01) | |
| *A61L 31/14* | (2006.01) | |
| *C08L 5/00* | (2006.01) | |
| *C08L 71/02* | (2006.01) | |
| *C09J 7/38* | (2018.01) | |
| *C09J 11/06* | (2006.01) | |
| *C09J 133/14* | (2006.01) | |
| *C09J 133/26* | (2006.01) | |

(52) U.S. Cl.
CPC .......... *C08L 33/26* (2013.01); *A61L 26/0052* (2013.01); *A61L 26/0071* (2013.01); *A61L 26/008* (2013.01); *A61L 31/041* (2013.01); *A61L 31/141* (2013.01); *A61L 31/145* (2013.01); *C08L 5/00* (2013.01); *C08L 71/02* (2013.01); *C09J 7/385* (2018.01); *C09J 11/06* (2013.01); *C09J 133/14* (2013.01); *C09J 133/26* (2013.01); *C08L 2203/02* (2013.01)

(58) Field of Classification Search
CPC ........ C08L 33/26; C08L 71/02; C08L 101/14; C08L 2203/02; A61L 26/0052; A61L 26/008; A61L 31/041; A61L 15/58; A61L 15/60; A61L 26/0071; A61L 31/141; A61L 31/145; C09J 7/385; C09J 133/14; C09J 133/26; C08F 220/56; C08F 220/58; C08F 222/385; C08K 5/0016
See application file for complete search history.

(56) References Cited

U.S. PATENT DOCUMENTS

| | | | | |
|---|---|---|---|---|
| 5,707,635 A | * | 1/1998 | Deckner | .................. A61P 25/20 424/59 |
| 2004/0191316 A1 | * | 9/2004 | Sasahara | ................ C09J 133/24 424/486 |

FOREIGN PATENT DOCUMENTS

| | | | |
|---|---|---|---|
| CN | 101843567 | | 9/2010 |
| EP | 0 588 238 A2 | | 3/1994 |
| JP | H06-256616 | | 9/1994 |
| JP | H10-028726 | | 2/1998 |
| JP | 2000281988 A | * | 10/2000 |
| JP | 2002-370025 | | 12/2002 |
| JP | 2010-222320 | | 10/2010 |
| JP | 2015-174847 | | 10/2015 |
| JP | 6209406 | | 9/2017 |

OTHER PUBLICATIONS

Machine translation into English of JP-2000281988-A; Minami et al. (Year: 2000).*
EESR issued in EP Patent Application No. 19777007.6, Dec. 2, 2021.
Office Action issued in Chinese Patent Application No. 201980016329. 8, May 28, 2021.
Office Action issued in EP Patent Application No. 19777007.6, Aug. 27, 2024.

* cited by examiner

*Primary Examiner* — Karuna P Reddy
(74) *Attorney, Agent, or Firm* — GREENBLUM & BERNSTEIN, P.L.C.

(57) ABSTRACT

The hydrogel of the present invention is a hydrogel comprising a polymer matrix, water and a plasticizer, wherein the hydrogel is characterized in that the plasticizer loss ratio is less than 2, the swelling rate is 115% or less when the hydrogel is exposed to the environment of 40° C. and 90% RH for 1 hour, and the initial adhesive force to a Bakelite plate is 100 gf/20 mm or more in the environment of 23° C. and 55% RH. The plasticizer is preferably polyoxyalkylene alkyl ether and/or sugar. The initial high adhesive force is retained by suppressing the swelling of the gel due to invasion of water from the outside and reducing the loss of a plasticizer.

3 Claims, 1 Drawing Sheet

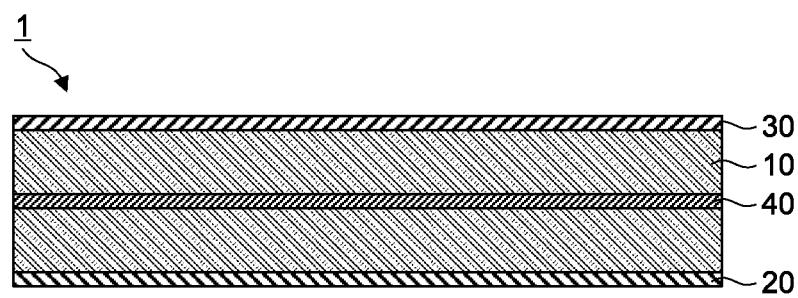

HYDROGEL

TECHNICAL FIELD

The present invention relates to a hydrogel. In particular, the present invention relates to a hydrogel preferably used as an adhesive material that is directly adhered to a living body.

BACKGROUND ART

Medical electrodes used in monitoring devices for electrocardiogram or in treatments using electrical stimulation such as low frequency or medium frequency, indifferent plates of cautery knives, and various types of adhesive tapes and wound covering materials, a hydrogel adhesive material is used in a portion thereof to be adhered to a living body.

As a conventional hydrogel, Patent Literature 1 discloses a hydrogel comprising a polymer matrix, water, and polyhydric alcohol such as polyethylene glycol, wherein the polymer matrix consists of (meth)acrylamide and a copolymer of another monofunctional monomer having one polymerizable carbon-carbon double bond in a molecule thereof and a crosslinkable monomer, wherein such another monofunctional monomer is at least one selected from the group consisting of diacetone (meth)acrylamide, N,N-dimethyl (meth)acrylamide, N-(meth)acryloylmorpholine, and N-(2-hydroxyethyl)(meth)acrylamide, and the crosslinkable monomer is at least one selected from the group consisting of divinylbenzene and divinylbiphenyl.

CITATION LIST

Patent Literature

Patent Literature 1: Japanese Patent No. 6209406

SUMMARY OF INVENTION

Technical Problem

In a high humidity environment, the above-described conventional hydrogel has easily absorbed water from the outside, the gel has easily swollen, and the adhesive force has been reduced in a short time in some cases. In addition, polyhydric alcohol that serves as a plasticizer contributing to adhesiveness has been lost from the gel, and the adhesive force of the gel has been thereby reduced. Hence, the conventional hydrogel has been problematic in that it is easily removed from the skin or device in a high humidity environment.

Under such circumstances, it is an object of the present invention to provide a hydrogel, in which the swelling of the gel due to invasion of water from the outside is suppressed and the initial high adhesive force is retained by reduction in the loss of a plasticizer.

Solution to Problem

In order to solve the above-described problems, the present inventors have used a compound having a relatively hydrophobic structure, specifically, have used polyoxyalkylene alkyl ether or sugar as a plasticizer, instead of using the conventional polyhydric alcohol, so that the inventors have found that the swelling of the gel and the loss of the plasticizer can be suppressed and the initial high adhesive force can be retained, thereby completing the present invention. Specifically, the gist of the present invention is as follows.

(1) A hydrogel comprising a polymer matrix, water and a plasticizer, in which the plasticizer loss ratio obtained by the below-mentioned evaluation method is less than 2, the swelling rate is 115% or less when the hydrogel is exposed to the environment of 40° C. and 90% RH for 1 hour, and the initial adhesive force to a Bakelite plate is 100 gf/20 mm or more in the environment of 23° C. and 55% RH.

(Method of Measuring Plasticizer Loss Ratio)

A hydrogel, which has been cut into a 40 mm square and the weight (g) of which has previously been measured, is dried in an oven at 120° C. for 120 minutes, and the weight (g) thereof is then measured. Then, according to the following equation, the loss rate of water existing in the hydrogel is calculated (G0). In addition, the gel whose weight (g) has previously been measured is immersed in ion exchange water at 20° C. for 60 minutes, and is then dried in an oven at 120° C. for 240 minutes, and thereafter, the weight (g) thereof is measured. Thereafter, according to the following equation, the loss rate of water existing in the hydrogel is calculated (G1). Furthermore, the plasticizer loss ratio is calculated according to the following equation.

$$\text{Plasticizer loss ratio} = G1/G0$$

$$\text{Water loss rate } (G0)(\%) = (\text{Weight of gel-weight of gel after drying})/\text{weight of gel} \times 100$$

$$\text{Water loss rate } (G1)(\%) = (\text{Weight of gel-weight of gel after water immersion and drying})/\text{weight of gel} \times 100$$

(2) The hydrogel according to the above (1), wherein the plasticizer is polyoxyalkylene alkyl ether and/or sugar.

(3) The hydrogel according to the above (2), wherein the polyoxyalkylene alkyl ether is at least one selected from the group consisting of polyoxyethylene methyl glucoside and polyoxyethylene alkyl ether, and the sugar is at least one selected from the group consisting of monosaccharide, disaccharide and polysaccharide.

(4) The hydrogel according to any one of the above (1) to (3), wherein the content of the plasticizer is 10% to 60% by weight, with respect to 100% by weight (total amount) of the hydrogel.

(5) The hydrogel according to any one of the above (1) to (4), wherein the polymer matrix is formed from a copolymer of a monofunctional monomer having one ethylenically unsaturated group and a crosslinkable monomer.

(6) The hydrogel according to the above (5), wherein the monofunctional monomer comprises at least one selected from the group consisting of a (meth)acrylamide monomer, a (meth)acrylic acid ester monomer, and (meth)acrylic acid or a salt thereof. It is to be noted that the term "(meth)acryl" is used in the present description to mean acryl or methacryl.

(7) The hydrogel according to the above (5), wherein the monofunctional monomer comprises at least one selected from the group consisting of (meth)acrylamide, diacetone (meth)acrylamide, (meth)acrylic acid, and tert-butylacrylamidesulfonic acid.

(8) The hydrogel according to any one of the above (1) to (7), wherein the adhesive force obtained after the hydrogel is exposed to the environment of 40° C. and 90% RH for 1 hour is 60% or more, with respect to the initial adhesive force.

(9) The hydrogel according to any one of the above (1) to (8), which is used as a medical electrode in monitoring devices or devices for performing treatments using electrical stimulation, an indifferent plate of a cautery knife, an adhesive tape, or a wound covering material.

The present description includes the content disclosed in Japanese Patent Application No. 2018-069422, from which the present application claims priority.

Advantageous Effects of Invention

According to the present invention, there can be obtained a hydrogel, in which the swelling of the gel due to moisture absorption is suppressed, and the loss of a plasticizer is suppressed, so that the initial high adhesive force can be retained without a reduction in the adhesive force. Accordingly, the hydrogel of the present invention is preferably used as an adhesive material to be adhered to a living body, and the removal thereof from the skin or device can be avoided upon the use thereof under the environment of sweat or high humidity.

BRIEF DESCRIPTION OF DRAWING

FIG. 1 is a cross-sectional view showing one embodiment of a gel sheet comprising the hydrogel according to the present invention.

DESCRIPTION OF EMBODIMENTS

Hereinafter, the present invention will be described in detail in the following embodiments.

The hydrogel of the present invention comprises a polymer matrix, water and a plasticizer. In addition, the hydrogel of the present invention is characterized in that the plasticizer loss ratio is less than 2, the swelling rate is 115% or less when the hydrogel is exposed to the environment of 40° C. and 90% RH for 1 hour, and the initial adhesive force to a Bakelite plate is 100 gf/20 mm or more in the environment of 23° C. and 55% RH. Preferably, the plasticizer loss ratio is less than 1.90, and the swelling rate is 110% or less. In addition, the initial adhesive force is preferably 200 gf/20 mm or more. By setting the plasticizer loss ratio and the swelling rate to be within the above-described ranges, invasion of water from the outside of the hydrogel is suppressed, and the initial high adhesive force can be maintained even in a high humidity environment in which sweat and the like adhere to the hydrogel. Specifically, the adhesive force of the hydrogel, after it has been exposed to the environment of 40° C. and 90% RH for 1 hour, is 60% or more, and preferably 70% or more, with respect to the initial high adhesive force thereof. Next, individual components constituting the present hydrogel will be described.

(Polymer Matrix)

The polymer matrix is not particularly limited, as long as it forms a network structure, and comprises at least water so that it can form gel. A synthetic polymer allowed to be adhered to the skin can be applied. As a preferred example, such a polymer matrix can be formed from a copolymer of a monofunctional monomer having one ethylenically unsaturated group and a crosslinkable monomer.

Examples of the monofunctional monomer that is preferably used herein may include monomers such as a (meth)acrylamide monomer, a (meth)acrylic acid ester monomer, and (meth)acrylic acid or a salt thereof. These compounds may be used alone or may also be used in combination of two or more types.

Specific examples of the (meth)acrylamide monomer may include: N,N-dialkyl(meth)acrylamide, such as (meth)acrylamide, N,N-dimethyl(meth)acrylamide and N,N-diethyl (meth)acrylamide; N-alkyl(meth)acrylamide, such as N-isopropyl(meth)acrylamide, N-methyl(meth)acrylamide, N-ethyl(meth)acrylamide, and N-propyl(meth)acrylamide; N-hydroxyalkyl(meth)acrylamide, such as N-hydroxyethyl (meth)acrylamide and N-hydroxymethyl(meth)acrylamide; amino group-containing cationic acrylamide compounds, such as dimethylaminopropyl(meth)acrylamide; sulfonic acid group-containing anionic monofunctional monomers or salts thereof, such as 4-acryloyl morpholine and tert-butylacrylamidesulfonic acid; and the derivatives thereof. These monofunctional monomers may be used alone or may also be used in combination of two or more types of monomers.

Specific examples of the (meth)acrylic acid ester may include: (meth)acrylic acid alkyl esters, in which the alkyl group contains 1 to 18 carbon atoms, such as methyl (meth)acrylate, ethyl (meth)acrylate, n-propyl (meth)acrylate, isopropyl (meth)acrylate, n-butyl (meth)acrylate, isobutyl (meth)acrylate, and tert-butyl (meth)acrylate; alkoxy group-containing (meth)acrylic acid esters including methoxy polyethylene glycol (meth)acrylate, such as 2-methoxyethyl (meth)acrylate, ethoxyethyl (meth)acrylate, and methoxy triethylene glycol (meth)acrylate; hydroxyalkyl (meth)acrylate (in which an aryl group may optionally bind to the hydroxyalkyl group via an ether bond), such as 2-hydroxyethyl (meth)acrylate and 2-hydroxypropyl (meth) acrylate; glycerin mono(meth)acrylate; polyalkylene glycol mono(meth)acrylate, such as polyethylene glycol mono (meth)acrylate and a polyethylene glycol-polypropylene glycol copolymer; and (meth)acrylic acid esters having an aromatic ring, such as benzyl (meth)acrylate. These monofunctional monomers may be used alone or may also be used in combination of two or more types of monomers.

Specific examples of the (meth)acrylic acid or a salt thereof may include acrylic acid, methacrylic acid, sodium acrylate, potassium acrylate, and potassium methacrylate. These monofunctional monomers may be used alone or may also be used in combination of two or more types of monomers.

The total content of the structural unit derived from the above-described monofunctional monomer in the hydrogel of the present invention is not particularly limited, and it is preferably within the range of 10% to 50% by weight, and is more preferably within the range of 15% to 45% by weight, with respect to 100% by weight (total amount) of the hydrogel. If the total content of the structural unit derived from the above-described monofunctional monomer in the hydrogel is too small, it is likely that the shape-retaining property of the hydrogel may become insufficient and thus, may become too soft or too fragile. On the other hand, if the total content of the structural unit derived from the above-described monofunctional monomer in the hydrogel is too large, it is likely that the hydrogel may become hard and the flexibility may be lost.

The crosslinkable monomer is not particularly limited, and it is preferably a compound having two or more carbon-carbon double bonds having polymerizability in the molecule thereof. Examples of the crosslinkable monomer may include divinylbenzene, divinylbiphenyl, N,N'-methylenebis(meth)acrylamide, ethylene glycol di(meth)acrylate, glycerin tri(meth)acrylate, polyethylene glycol di(meth) acrylate, polypropylene glycol di(meth)acrylate, and polyglycerin di(meth)acrylate. These compounds may be used alone or may also be used in combination of two or more types.

The content of the structural unit derived from the above-described crosslinkable monomer in the hydrogel of the present invention is not particularly limited, and it depends on the types of the monofunctional monomer and the crosslinkable monomer used. The content of the structural unit derived from the above-described crosslinkable monomer is preferably within the range of 0.01% to 0.5% by weight, and is more preferably within the range of 0.01% to 0.1% by weight, with respect to 100% by weight (total amount) of the hydrogel. If the content of the structural unit derived from the above-described crosslinkable monomer in the hydrogel is too small, it is likely that the crosslink density may decrease and the shape stability of the gel may become poor. On the other hand, the content of the structural unit derived from the above-described crosslinkable monomer in the hydrogel is too large, the hydrogel may easily become a hard and fragile gel.

(Water)

The hydrogel of the present invention comprises water. The content of the water in the present hydrogel is not particularly limited. In order to ensure preferred adhesive properties or electric properties, the content of the water is preferably within the range of 10% to 60% by weight, and is more preferably within the range of 15% to 50% by weight, with respect to 100% by weight (total amount) of the hydrogel. If the content of the water in the hydrogel is too small, since the water content to the equilibrium water content of the gel is too small, it is likely that the absorbency of the hydrogel may become high and the gel may degenerate over time. On the other hand, if the content of the water in the hydrogel is too large, since a difference between the water content and the equilibrium water content of the gel becomes large, it is likely that the gel may shrink due to drying or the physical properties may change.

(Plasticizer)

The plasticizer imparts moisture retention power to the hydrogel, suppresses transpiration of water, and retains the flexibility of the gel. As such a plasticizer, a compound, which relatively exhibits hydrophobicity (which is hydrophilic as an absolute index, though), rather than the conventional polyhydric alcohol such as glycerin, can be used. Specifically, polyoxyalkylene alkyl ether and/or sugar are preferably used. These compounds have a composition more hydrophobic than polyhydric alcohol, and thus, it can prevent invasion of water from the outside into the hydrogel and can suppress the swelling of the gel.

As a polyoxyalkylene alkyl ether, a straight-chain type polyoxyalkylene alkyl ether represented by the following formula:

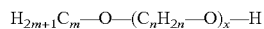

$$H_{2m+1}C_m-O-(C_nH_{2n}-O)_x-H$$

is applicable. In the above formula, it is preferable that m be in the range of 1 to 20, n be in the range of 2 to 3, and x be in the range of 2 to 50. Specific examples of the straight-chain type polyoxyalkylene alkyl ether may include: polyoxyethylene alkyl ethers, such as polyoxyethylene lauryl ether, polyoxyethylene stearyl ether, and polyoxyethylene isostearyl ether; and polyoxypropylene alkyl ethers, such as polyoxypropylene lauryl ether, polyoxypropylene stearyl ether, and polyoxypropylene isostearyl ether.

Other examples of the polyoxyalkylene alkyl ether that can be applied herein may include cyclic (multi-chain type) polyoxyalkylene alkyl ethers, such as polyoxyethylene methyl glucoside and polyoxypropylene methyl glucoside. These straight-chain type or multi-chain type polyoxyalkylene alkyl ethers may be used alone as a single type or in combination of two or more types.

Moreover, as sugar, one or more types selected from the group consisting of monosaccharide, disaccharide and polysaccharide can be used. Examples of the monosaccharide may include xylose, arabinose, glucose, galactose, and mannose. Examples of the disaccharide may include sucrose, maltose, cellobiose, and lactose. Examples of the polysaccharide may include oligosaccharide such as maltotriose, xylan, starch, cellulose, chitin, and chitosan. Amino sugars of these sugars and the N-acetylated products thereof can also be applied. These sugars may be used in combination of any two or more types, regardless of D-form or L-form.

The content of the plasticizer is not particularly limited, and it depends on the type of the plasticizer. The content of the plasticizer is preferably in the range of 10% to 60% by weight, and is particularly preferably within the range of 20% to 50% by weight, with respect to 100% by weight (total amount) of the hydrogel. If the content of the plasticizer in the hydrogel it too small, the moisture retention power of the gel is poor, and thus, transpiration of water becomes significant. Hence, since the gel becomes poor in terms of temporal stability and flexibility, it is likely that the gel could not maintain the adhesive force. On the other hand, if the content of the plasticizer in the hydrogel it too large, it is likely that the plasticizer may bleed out on the surface of the gel.

The content ratio between the polymer matrix and the plasticizer is not particularly limited, and it is preferably in the range of 0.25:1 to 3.0:1, and is more preferably in the range of 0.45:1 to 2.5:1, at a weight ratio.

(Water-Soluble Polymer)

A water-soluble polymer may be added to the hydrogel of the present invention, as necessary. The applicable water-soluble polymer is not particularly limited, and examples of the water-soluble polymer may include: a single polymer of vinyl pyrrolidone (i.e., polyvinyl pyrrolidone); vinyl pyrrolidone copolymers, such as a copolymer of vinyl alcohol and vinyl pyrrolidone, a copolymer of ether-modified vinyl alcohol and vinyl pyrrolidone, and a copolymer of vinyl pyrrolidone and vinyl acetate; and polyvinyl alcohol, polyacrylic acid, sodium polyacrylate, carboxymethyl cellulose sodium, hydroxyethyl cellulose, hydroxypropyl cellulose, sodium alginate, and dextran. These water-soluble polymers may be used alone as a single type or in combination of two or more types.

Among such water-soluble polymers, polyacrylic acid and/or sodium polyacrylate are particularly excellent in terms of the effect of imparting adhesiveness to the hydrogel. In the case of allowing the hydrogel of the present invention to comprise polyacrylic acid and/or sodium polyacrylate, the content of the polyacrylic acid and/or the sodium polyacrylate (in the case of allowing the present hydrogen to comprise both polyacrylic acid and sodium polyacrylate, the content indicates the total content) is preferably in the range of 0.1% to 5% by weight, with respect to 100% by weight (total amount) of the hydrogel. If the content of the water-soluble polymer in the hydrogel is too large, it becomes difficult to handle the hydrogel due to an increase in the viscosity of the entire system, and also, effects that meet the additive amount of the water-soluble polymer cannot be obtained.

(Electrolyte)

An electrolyte may be added to the hydrogel of the present invention, as necessary. By adding such an electrolyte to the hydrogel, conductivity can be imparted to the hydrogel. Such a conductivity-imparted hydrogel can be preferably used for bioelectrodes, such as electrodes for electrocardiogram measurement, electrodes for low frequency treatment devices, or various types of ground electrodes. When the present hydrogel is used as a hydrogel for bioelectrodes, the resistivity of the hydrogel comprised in the electrolyte is preferably within the range of 0.01 to 100 kΩ·cm.

The above-described electrolyte is not particularly limited, and it may be, for example, a salt. Examples of such a salt may include: halogenated alkali metals, such as sodium halide (e.g., sodium chloride), lithium halide, and potassium halide; halogenated alkaline-earth metals, such as magnesium halide and calcium halide; other metal halides; the hypochlorite, chlorite, chlorate, perchlorate, sulfate, carbonate, nitrate, and phosphate of various types of metals; inorganic salts, such as ammonium salts and various types of complex salts; the salts of monovalent organic carboxylic acids, such as acetic acid, benzoic acid, and lactic acid; the monovalent, divalent or more-valent salts of polycarboxylic acids, such as tartaric acid, phthalic acid, succinic acid, adipic acid, and citric acid; the metal salts of organic acids, such as sulfonic acid and amino acid; organic ammonium salts; and the salts of polymer electrolytes, such as poly(meth)acrylic acid, polyvinylsulfonic acid, poly(tert-butylacrylamidesulfonic acid), polyallylamine, and polyethylenimine.

Furthermore, the above-described electrolyte may be a substance having properties by which it is insoluble when it is mixed into the hydrogel, it is in a dispersed state during preparation of a mixed solution, and it is dissolved in the hydrogel over time. Examples of such an electrolyte may include silicate, aluminate, metal oxide, and hydroxide.

When conductivity is imparted to the hydrogel of the present invention, the content of the above-described electrolyte in the hydrogel is preferably in the range of 0.001% to 10% by weight, and is more preferably in the range of 0.1% to 5% by weight, with respect to 100% by weight (total amount) of the hydrogel. A water-containing hydrogel originally has properties as a dielectric. When the water-containing hydrogel is combined with an electrode element to produce an electrode, the electrode has capacitance that depends on the thickness of the gel or the area of the electrode element. However, the impedance (Z) of the electrode is largely influenced by the concentration of an electrolyte, in particular, in a low frequency region of less than 1 kHz. If the content of the above-described electrolyte in the hydrogel is less than 0.001% by weight, the impedance becomes high, and the hydrogel may not be preferable for intended use regarding conductivity in some cases. On the other hand, if the content of the above-described electrolyte in the hydrogel is too large, it becomes difficult for the electrolyte to be dissolved in the hydrogel, and as a result, crystals may be precipitated in the gel or the electrolyte may inhibit dissolution of other components in the hydrogel in some cases. In addition, too large content of the electrolyte causes conductivity to reach its limit, and from the viewpoint of imparting conductivity to the hydrogel, addition of an excessively large amount of electrolyte is not considered to be advantageous.

The above-described electrolyte may also be used for purposes other than addition of conductivity to the hydrogel. For example, acid salts, basic salts, or multifunctional salts may be added to the hydrogel for the purpose of adjusting the pH of the hydrogel. Moreover, the above-described electrolyte may be added for the purpose of improving the moisturizing performance of the hydrogel or giving antibacterial properties to the hydrogel.

(Other Additives)

An antiseptic, a germicide, a rust inhibitor, an antioxidant, a stabilizer, a perfume, a surfactant, a coloring agent, an anti-inflammatory agent, a vitamin agent, and medicinal ingredients such as a whitening agent may be added, as appropriate, to the hydrogel of the present invention, unless they inhibit the effects of the present invention. These additives may be used alone or may also be used in combination of two or more types. In addition, these additives can be used in the range of 0.01% to 10% by weight with respect to 100% by weight (total amount) of the hydrogel.

(Method for Producing Hydrogel)

When the polymer matrix is composed of a monofunctional monomer and a crosslinkable monomer, the hydrogel of the present invention can be easily produced according to a production method comprising using a mixed solution prepared by uniformly mixing and dissolving components constituting the polymer matrix and a plasticizer into water, and copolymerizing the monofunctional monomer with the crosslinkable monomer in the mixed solution. The mixed solution may comprise the aforementioned water-soluble polymer, electrolyte, and/or various types of additives, as necessary.

Alternatively, the hydrogel of the present invention can also be produced according to a production method comprising impregnating a polymer matrix formed by previously polymerizing a monofunctional monomer with a crosslinkable monomer with water, a plasticizer, and as necessary, the aforementioned water-soluble polymer, electrolyte, and/or various types of additives.

Polymerization of a monofunctional monomer with a crosslinkable monomer is preferably carried out in the presence of a polymerization initiator. For example, such a polymerization initiator is preferably added to the above-described mixed solution. The polymerization initiator is not particularly limited, and examples of the polymerization initiator may include a thermal polymerization initiator and a photopolymerization initiator.

The above-described thermal polymerization initiator is not particularly limited, as long as it is cleaved by heat to generate radicals. Examples of the thermal polymerization initiator may include: organic peroxides such as benzoyl peroxide; azo-polymerization initiators, such as azobiscyanovaleric acid, azobis(isobutyronitrile), and azobis(amidinopropane) dihydrochloride; and persulfates, such as potassium persulfate and ammonium persulfate. These thermal polymerization initiators may be used alone or may also be used in combination of two or more types. Moreover, as necessary, such a thermal polymerization initiator may be used in combination with a redox initiator consisting of a reducer such as ferrous sulfate or pyrosulfite and a peroxide such as hydrogen peroxide, sodium thiosulfate or peroxodisulfate.

The above-described thermal photopolymerization initiator is not particularly limited, as long as it is cleaved by ultraviolet light or visible light to generate radicals. Examples of the thermal photopolymerization initiator may include azo-polymerization initiators, such as 2,2'-azobis-N-(2-hydroxyethyl)propionamide and 2,2'-azobis(1-imino-1-pyrrolidino-2-methylpropane) dihydrochloride, α-hydroxyketone, α-aminoketone, benzyl methyl ketal, bisacylphosphine oxide, and metallocene. More specific examples may include 1-[4-(2-hydroxyethoxy)-phenyl]-2-hydroxy-2-methyl-propan-1-one (product name: IRGACURE (registered trademark) 2959, manufactured by BASF Japan), 2-hydroxy-2-methyl-1-phenyl-propan-1-one (product name: Darocur (registered trademark) 1173, manufactured by BASF Japan), 1-hydroxy-cyclohexyl-phenyl-ketone (product name: IRGACURE (registered trademark) 184, manufactured by BASF Japan), 2-methyl-1-[(methylthio)phenyl]-2-morpholinopropan-1-one (product name: IRGACURE (registered trademark) 907, manufactured by BASF Japan), and 2-benzyl-2-dimethylamino-1-(4-morpholinophenyl)-butan-1-one (product name: IRGACURE (registered trademark) 369, manufactured by BASF Japan). These photopolymerization initiators may be used alone or may also be used in combination of two or more types.

The above-described polymerization initiator is used in an amount of preferably 0.01 to 1.0% by weight, and more preferably 0.05 to 0.5% by weight, with respect to 100% by weight (total amount) of the obtained hydrogel (i.e., the total amount of the above-described mixed solution). If the amount of the polymerization initiator used is 0.01% by weight or more with respect to 100% by weight (total amount) of the obtained hydrogel (i.e., the total amount of the above-described mixed solution), the polymerization reaction sufficiently progresses, and the amounts of the monofunctional monomer and the crosslinkable monomer remaining in the obtained hydrogel can be reduced. On the other hand, if the amount of the polymerization initiator used is 1.0% by weight or less with respect to 100% by weight (total amount) of the obtained hydrogel (i.e., the total amount of the above-described mixed solution), discoloration (yellowness) or odor caused by the polymerization initiator remaining in the obtained hydrogel can be prevented.

The method of polymerizing a monofunctional monomer with a crosslinkable monomer is not particularly limited, and it is, for example, a method of performing heating, light irradiation or radiation exposure on a mixture (mixed solution) comprising a monofunctional monomer, a crosslinkable monomer and the like. Specific examples of the polymerization method may include: a method comprising adding a thermal polymerization initiator as a polymerization initiator to the aforementioned mixture, and then heating the obtained mixture to polymerize the monofunctional monomer with the crosslinkable monomer in the mixture; a method comprising adding a photopolymerization initiator as a polymerization initiator to the aforementioned mixture, and then performing light irradiation (ultraviolet light or visible light irradiation) on the obtained mixture to polymerize the monofunctional monomer with the crosslinkable monomer in the mixture; a method comprising adding a thermal polymerization initiator and a photopolymerization initiator as polymerization initiators to the aforementioned mixture, and then performing simultaneously light irradiation and heating on the obtained mixture, so as to polymerize the monofunctional monomer with the crosslinkable monomer in the mixture; and a method comprising applying radiation such as electron beam or gamma rays to the aforementioned mixture, so as to polymerize the monofunctional monomer with the crosslinkable monomer in the mixture. Besides, when a redox initiator is used in combination as a thermal polymerization initiator, the reaction can be carried out even without heating. However, in order to reduce the amount of residual monomers or the reaction time, it is preferable to perform heating even in the case of using such a redox initiator in combination. Moreover, as mentioned above, it is possible to perform expose radiation exposure on the aforementioned mixture, so as to polymerize the monofunctional monomer with the crosslinkable monomer in the mixture. However, this method requires special equipment for radiation exposure. Thus, as a method of polymerizing the monofunctional monomer with the crosslinkable monomer in the mixture, a method of performing heating or light irradiation on the mixture is preferable, and from the viewpoint of being capable of obtaining a gel with stable physical properties, a method of performing light irradiation on the mixture is more preferable.

In the case of adding a photopolymerization initiator to the aforementioned mixture and then performing polymerization according to ultraviolet light irradiation, the integrated amount of the ultraviolet light applied is preferably 1000 mJ/cm$^2$ or more.

In the case of producing the hydrogel of the present invention, the used amount of the components other than the monofunctional monomer and the crosslinkable monomer (e.g., a plasticizer, water, a water-soluble polymer, an electrolyte, and other additives), with respect to the total weight of the components used in the production of the hydrogel (e.g., the monofunctional monomer, the crosslinkable monomer, the plasticizer, water, the water-soluble polymer, the electrolyte, and other additives) (i.e., the weight of the above-described mixed solution), is equal to the content of the components other than the monofunctional monomer and the crosslinkable monomer in the hydrogel of the present invention. In addition, the used amount of the monofunctional monomer and the crosslinkable monomer with respect to the total weight of the components used in the production of the hydrogel (i.e., the weight of the above-described mixed solution) is equal to the content of the monofunctional monomer and the crosslinkable monomer in the hydrogel of the present invention. For example, the content of the monofunctional monomer in the above-described mixed solution is equal to the content of the structural unit derived from the monofunctional monomer in the hydrogel of the present invention. Moreover, the content of the crosslinkable monomer in the above-described mixed solution is equal to the content of the structural unit derived from the crosslinkable monomer in the hydrogel of the present invention. Furthermore, the total content of the monofunctional monomer and the crosslinkable monomer in the above-described mixed solution is equal to the content of the polymer matrix in the hydrogel of the present invention.

FIG. 1 shows a cross-section of one embodiment of a gel sheet comprising the hydrogel according to the present invention. In a gel sheet 1 of the present embodiment, a base film 20 and a top film 30, which are used to protect a hydrogel 10, are laminated on both surfaces of the sheet-like hydrogel 10. The thickness of the hydrogel 10 can be determined, as appropriate, depending on the intended use of the gel sheet 1. For example, when the gel sheet 1 is used by being attached to a living body, the thickness of the hydrogel 10 is preferably set within the range of 0.01 mm to 2.0 mm.

Examples of the base film 20 that can be used herein may include a resin film consisting of a resin such as polyester (e.g., polyethylene terephthalate (PET)), polyolefin (e.g., polypropylene), polystyrene or polyurethane, a paper, and a paper formed by lamination of the above-described resin films. The surface of such a base film 20 that is contacted with the hydrogel 10 is preferably subjected to a mold release treatment such as silicone coating. Specifically, when the above-described base film 20 is used as a release paper, a resin film consisting of a resin (e.g., polyester, polyolefin, polystyrene, etc.) a paper, or a paper prepared by lamination of the above-described resin films, on the surface of which a mold release treatment has been performed, can be preferably used as a base film 20. The above-described base film, on which a mold release treatment is performed, is particularly preferably a biaxially oriented PET film, a biaxially oriented polypropylene (OPP) film, or the like. The mold release treatment method may be, for example, silicone coating, and it is particularly preferably baking-type silicone coating involving a crosslinking hardening reaction using heat or ultraviolet light.

When the base film 20 is used not as a release paper but as a backing material (lining material) of the hydrogel 10, it is preferable to use a polyester film, a polyolefin film, a polystyrene film, a polyurethane film or the like without being subjected to a mold release treatment. Among these films, a polyurethane film is particularly preferable because it has flexibility and may have water vapor permeability. In addition, since such a polyurethane film itself is generally too soft and thus, it is hardly handled in the production step, it is preferably used by being laminated with a carrier film such as a polyolefin film or a paper. In this case, the step of generating the hydrogel is preferably carried out in a state in which a carrier film is attached to the base film.

As a top film 30, it is possible to use a film having the same material as that of the base film 20. However, in order not to prevent photopolymerization, a film formed with a material that does not block light is preferably selected. Moreover, a film used as a backing material (lining material) is preferably not to be used as a top film 30. In particular, in a case where the film used as a backing material is likely to be deteriorated by irradiation with ultraviolet light or the like, if the film used as a backing material is used as a top film 30, the film used as a backing material is unfavorably positioned on the side directly irradiated with ultraviolet light.

Moreover, in the present embodiment, for the purpose of improving the tear strength and handling ability of the hydrogel 10, an intermediate base material 40 consisting of a woven fabric or a non-woven fabric is embedded along the planar direction of the hydrogel 10. Examples of the material of such a non-woven fabric and a woven fabric that can be used herein may include: natural fibers such as cellulose, silk, and hemp; synthetic fibers such as polyester, nylon, rayon, polyethylene, polypropylene, and polyurethane; and mixed fabrics thereof. A binder may be used for such a non-woven fabric and a woven fabric, as necessary, and the non-woven fabric and a woven fabric may be further colored, as necessary.

The method for producing the above-described non-woven fabric is not particularly limited, and examples of the production method may include a dry method, a wet method, a spunbond method, a melt-blown method, an air-laid method, a chemical bond method, a thermal bond method, a needle punch method, and a water-jet interlacing method. For the position control of the intermediate base material 40, it is preferable to adopt a production method that is suitable for weight or material, and not to cause uneven weight. In the case of a woven fabric as well, the material thereof is not particularly limited to plain weave, tricot, Russell, etc., and it can be selected, as appropriate.

The weight of the above-described woven fabric or non-woven fabric is not particularly limited, as long as it can provide the desired physical properties of the intermediate base material 40. For example, the weight is preferably within the range of 10 to 40 $g/m^2$, and is more preferably within the range of 10 to 28 $g/m^2$. If the weight of the above-described woven fabric and non-woven fabric is too small, it cannot reinforce the hydrogel 10, or uneven weight may increase and the permeability of a liquid may change depending on location upon the production of the hydrogel 10, so that the position of the intermediate base material 40 may be changed. On the other hand, if the weight of the above-described woven fabric and non-woven fabric is too large, the intermediate base material 40 becomes hard, so that the followability of the hydrogel 10 to the skin may be impaired. Therefore, the weight of the woven fabric or non-woven fabric is determined, as appropriate, while taking into consideration the balance among these factors.

If the thickness of the intermediate base material 40 is too thick, the permeability of the liquid may be deteriorated in some cases. In contrast, if the thickness of the intermediate base material 40 is too thin, it may become impossible to reinforce the hydrogel 10, or the position of the intermediate base material 40 may be changed, as in the case of an excessively small weight. Thus, the thickness of the intermediate base material 40 is determined, while taking into consideration these factors. The thickness of the intermediate base material 40 is preferably within the range of 0.05 to 2.0 mm. In addition, the thickness is more preferably 0.05 to 0.5 mm, and particularly preferably 0.08 to 0.3 mm.

The method for producing the gel sheet 1 is not particularly limited, and conditions of the production method are changed depending on the composition of the hydrogel 10, the material and thickness of the intermediate base material 40, and the like. Examples of the method for producing the gel sheet 1 that can be applied herein, as appropriate, may include: a method for obtaining the gel sheet 1, comprising retaining the intermediate base material 40 on the upper side of the base film 20, while applying a constant tension to the intermediate base material 40, then pouring a gel composition prepared by mixing individual components with one another onto the upper side and lower side of the intermediate base material 40, then covering the intermediate base material with the top film 30, and then crosslinking and hardening the hydrogel 10 by light irradiation and/or heating; and a method for obtaining the gel sheet 1, comprising producing two hydrogels whose surface is smooth, then sandwiching the intermediate base material 40 that is retained while a constant tension is applied thereto, by these hydrogels, and then laminating the base film 20 and the top film 30 on both surfaces.

In the aforementioned hydrogel of the present invention, the swelling thereof due to invasion of water from the outside can be suppressed, and the initial high adhesive force thereof can be maintained even in a high humidity environment. Therefore, the hydrogel of the present invention has resistance to sweat and the like, and can be preferably used as a hydrogel that is used by being attached to a living body, for example, as a hydrogel used in monitoring devices such as an electrocardiograph, medical electrodes used in devices for performing treatments using electrical stimulation such as low frequency or medium frequency, indifferent plates of cautery knives, and various types of adhesive tapes and wound covering materials.

EXAMPLES

Hereinafter, the present invention will be described in more detail in the following examples and comparative examples. However, these examples are not intended to limit the scope of the present invention.

Example 1

15 Parts by weight of acrylamide (which is abbreviated as "AAM," manufactured by Mitsubishi Chemical Corporation), 15 parts by weight of diacetoneacrylamide (which is abbreviated as "DAAM," manufactured by Nihon Kasei CO., LTD.), 0.06 parts by weight of N,N'-methylenebisacrylamide (which is abbreviated as "MBAA," manufactured by MRC UNITEC Co., Ltd.) used as a crosslinkable monomer, 42.79 parts by weight of polyoxyethylene methyl glucoside (Methyl Gluceth-20; model No. "MG-20E"; manufactured by NOF Corporation; n(=a+b+c+d) in formula (1) is 20) shown in the following formula (1) as a plasticizer, 25 parts by weight of ion exchange water, 2 parts by weight of sodium chloride used as an electrolyte, and 0.15 parts by weight of 1-[4-(2-hydroxyethoxy)-phenyl]-2-hydroxy-2-methyl-1-propan-1-one (product name: "IRGACURE (registered trademark) 2959," manufactured by BASF Japan) were mixed with one another, followed by stirring and dissolution, so as to obtain a mixed solution.

[Formula 1]

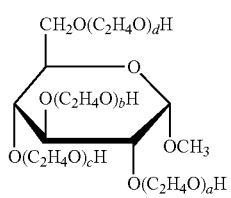

(1)

Subsequently, the obtained mixed solution was added dropwise onto a silicone-coated PET film (base film) with a thickness of 100 μm, and a nylon woven fabric and a silicone-coated PET film (top film) with a thickness of 38 μm were then covered onto the dropped mixed solution. Thereafter, the mixed solution was uniformly extended and was then fixed to a gel thickness of 0.75 mm. After that, using a metal halide lamp, this mixed solution was irradiated with ultraviolet light at an amount of energy of 3000 mJ/cm$^2$, so as to obtain a sheet-like hydrogel (gel sheet) with a thickness of 0.75 mm.

Example 2

A sheet-like hydrogel was obtained in the same manner as that of the above-described Example 1, with the exception that 42.79 parts by weight of polyoxyethylene methyl glucoside (Methyl Gluceth-10; model No. "MG-10E"; manufactured by NOF Corporation; n(=a+b+c+d) in the formula is 10) was used as a plasticizer, instead of MG-20E.

Example 3

A sheet-like hydrogel was obtained in the same manner as that of the above-described Example 1, with the exception that 42.79 parts by weight of polyoxyethylene lauryl ether (product name: "Nonion K-230," manufactured by NOF CORPORATION) was used as a plasticizer, instead of MG-20E.

Example 4

A sheet-like hydrogel was obtained in the same manner as that of the above-described Example 1, with the exceptions that 21.12 parts by weight of sucrose that was a disaccharide was used as a plasticizer, instead of MG-20E, and that the amount of ion exchange water was changed to 46.67 parts by weight.

Example 5

A sheet-like hydrogel was obtained in the same manner as that of the above-described Example 1, with the exception that 15 parts by weight of 4-hydroxybutyl acrylate (which is abbreviated as "4HBA," manufactured by Nihon Kasei CO., LTD.) was used, instead of diacetone acrylamide (DAAM).

Example 6

A sheet-like hydrogel was obtained in the same manner as that of the above-described Example 1, with the exceptions that the mixed amount of acrylamide (AAM) was changed to 12.5 parts by weight, that the mixed amount of diacetone acrylamide (DAAM) was changed to 12.5 parts by weight, that the mixed amount of N,N'-methylenebisacrylamide (MBAA) was changed to 0.05 parts by weight, and that the mixed amount of polyoxyethylene methyl glucoside (MG-20E) used as a plasticizer was changed to 47.8 parts by weight.

Example 7

A sheet-like hydrogel was obtained in the same manner as that of the above-described Example 1, with the exceptions that the mixed amount of acrylamide (AAM) was changed to 14 parts by weight, that the mixed amount of diacetone acrylamide (DAAM) was changed to 14 parts by weight, that the mixed amount of N,N'-methylenebisacrylamide (MBAA) was changed to 0.056 parts by weight, and that the mixed amount of polyoxyethylene methyl glucoside (MG-20E) used as a plasticizer was changed to 44.794 parts by weight.

Example 8

A sheet-like hydrogel was obtained in the same manner as that of the above-described Example 1, with the exceptions that the mixed amount of acrylamide (AAM) was changed to 17.5 parts by weight, that the mixed amount of diacetone acrylamide (DAAM) was changed to 17.5 parts by weight, that the mixed amount of N,N'-methylenebisacrylamide (MBAA) was changed to 0.07 parts by weight, and that the mixed amount of polyoxyethylene methyl glucoside (MG-20E) used as a plasticizer was changed to 37.78 parts by weight.

Example 9

A sheet-like hydrogel was obtained in the same manner as that of the above-described Example 1, with the exceptions that the mixed amount of acrylamide (AAM) was changed to 20 parts by weight, that the mixed amount of diacetone acrylamide (DAAM) was changed to 20 parts by weight, that the mixed amount of N,N'-methylenebisacrylamide (MBAA) was changed to 0.08 parts by weight, and that the mixed amount of polyoxyethylene methyl glucoside (MG-20E) used as a plasticizer was changed to 32.77 parts by weight.

Example 10

A sheet-like hydrogel was obtained in the same manner as that of the above-described Example 1, with the exceptions that the mixed amount of polyoxyethylene methyl glucoside (MG-20E) used as a plasticizer was changed to 21.12 parts by weight, and that the mixed amount of ion exchange water was changed to 46.67 parts by weight.

Example 11

A sheet-like hydrogel was obtained in the same manner as that of the above-described Example 1, with the exceptions that the mixed amount of polyoxyethylene methyl glucoside (MG-20E) used as a plasticizer was changed to 47.45 parts by weight, and that the mixed amount of ion exchange water was changed to 20.34 parts by weight.

Example 12

A sheet-like hydrogel was obtained in the same manner as that of the above-described Example 1, with the exceptions that the mixed amount of polyoxyethylene methyl glucoside (MG-20E) used as a plasticizer was changed to 54.23 parts by weight, and that the mixed amount of ion exchange water was changed to 13.56 parts by weight.

Example 13

A sheet-like hydrogel was obtained in the same manner as that of the above-described Example 1, with the exceptions that the mixed amount of N,N'-methylenebisacrylamide (MBAA) was changed to 0.03 parts by weight, and that the mixed amount of polyoxyethylene methyl glucoside (MG-20E) used as a plasticizer was changed to 42.82 parts by weight.

Example 14

A sheet-like hydrogel was obtained in the same manner as that of the above-described Example 1, with the exceptions that the mixed amount of N,N'-methylenebisacrylamide (MBAA) was changed to 0.09 parts by weight, and that the mixed amount of polyoxyethylene methyl glucoside (MG-20E) used as a plasticizer was changed to 42.76 parts by weight.

Example 15

A sheet-like hydrogel was obtained in the same manner as that of the above-described Example 1, with the exceptions that the mixed amount of N,N'-methylenebisacrylamide (MBAA) was changed to 0.2 parts by weight, and that the mixed amount of polyoxyethylene methyl glucoside (MG-20E) used as a plasticizer was changed to 42.65 parts by weight.

Example 16

A sheet-like hydrogel was obtained in the same manner as that of the above-described Example 1, with the exceptions that 15 parts by weight of acrylic acid (which is abbreviated as "AA," manufactured by Wako Pure Chemical Industries, Ltd.) was used instead of diacetone acrylamide (DAAM).

Example 17

A sheet-like hydrogel was obtained in the same manner as that of the above-described Example 1, with the exceptions that 15 parts by weight of N,N-dimethylacrylamide (which is abbreviated as "DMAA," manufactured by KJ Chemicals Corporation) was used instead of diacetone acrylamide (DAAM).

Example 18

A sheet-like hydrogel was obtained in the same manner as that of the above-described Example 1, with the exceptions that 15 parts by weight of N,N-diethylacrylamide (which is abbreviated as "DEAA," manufactured by KJ Chemicals Corporation) was used instead of diacetone acrylamide (DAAM).

Example 19

A sheet-like hydrogel was obtained in the same manner as that of the above-described Example 1, with the exceptions that 15 parts by weight of acryloyl morpholine (which is abbreviated as "ACMO," manufactured by KOHJIN Co., Ltd.) was used instead of diacetone acrylamide (DAAM), that the mixed amount of polyoxyethylene methyl glucoside (MG-20E) used as a plasticizer was changed to 33.895 parts by weight, and that the mixed amount of ion exchange water was changed to 33.895 parts by weight.

Example 20

A sheet-like hydrogel was obtained in the same manner as that of the above-described Example 1, with the exception that 15 parts by weight of methoxypolyethylene glycol acrylate (which is abbreviated as "AME-400," manufactured by NOF CORPORATION) was used instead of diacetone acrylamide (DAAM).

Example 21

A sheet-like hydrogel was obtained in the same manner as that of the above-described Example 1, with the exception that 15 parts by weight of diacetone acrylamide (DAAM), 15 parts by weight of N-t-butylacrylamidesulfonic acid (which is abbreviated as "TBAS," manufactured by MRC UNITEC Co., Ltd.), 39.99 parts by weight of polyoxyethylene methyl glucoside (MG-20E) serving as a plasticizer, 5.84 parts by weight of 48% sodium hydroxide aqueous solution for the adjustment of pH, and 21.96 parts by weight of ion exchange water were used.

Example 22

A sheet-like hydrogel was obtained in the same manner as that of the above-described Example 1, with the exception that 15 parts by weight of acrylic acid (AA), 15 parts by weight of N-t-butylacrylamidesulfonic acid (which is abbreviated as "TBAS," manufactured by MRC UNITEC Co., Ltd.), 29.52 parts by weight of polyoxyethylene methyl glucoside (MG-20E) serving as a plasticizer, 9.1 parts by weight of 48% sodium hydroxide aqueous solution for the adjustment of pH, and 29.17 parts by weight of ion exchange water were used.

Comparative Example 1

A sheet-like hydrogel was obtained in the same manner as that of the above-described Example 1, with the exception that 42.79 parts by weight of polyoxypropylene methyl glucoside (product name: "MACBIOBRIDE"; model No. "MG-10P"; manufactured by NOF Corporation; n(=a+b+c+d) in formula (2) is 10) was used as a plasticizer, instead of polyoxyethylene methyl glucoside (MG-20E).

[Formula 2]

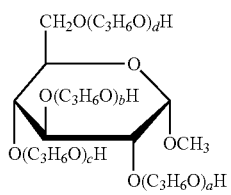

(2)

Comparative Example 2

A sheet-like hydrogel was obtained in the same manner as that of the above-described Example 1, with the exception that 42.79 parts by weight of sorbitol that was sugar alcohol was used as a plasticizer, instead of polyoxyethylene methyl glucoside (MG-20E).

Comparative Example 3

A sheet-like hydrogel was obtained in the same manner as that of the above-described Example 1, with the exception that 42.79 parts by weight of glycerin was used as a plasticizer, instead of polyoxyethylene methyl glucoside (MG-20E).

Comparative Example 4

A sheet-like hydrogel was obtained in the same manner as that of the above-described Example 1, with the exception that 42.79 parts by weight of polyethylene glycol (PEG, polymerization degree=300) was used as a plasticizer, instead of polyoxyethylene methyl glucoside (MG-20E).

Comparative Example 5

A sheet-like hydrogel was obtained in the same manner as that of the above-described Example 1, with the exceptions that the mixed amount of polyoxyethylene methyl glucoside (MG-20E) used as a plasticizer was changed to 61.01 parts by weight, and that the mixed amount of ion exchange water was changed to 6.78 parts by weight.

Comparative Example 6

A sheet-like hydrogel was obtained in the same manner as that of the above-described Comparative Example 4, with the exceptions that the mixed amount of acrylamide (AAM) was changed to 10 parts by weight, that the mixed amount of polyethylene glycol (PEG, polymerization degree=300) was changed to 33.94 parts by weight, that the mixed amount of sodium chloride was changed to 0.5 parts by weight, that the mixed amount of the photopolymerization initiator was changed to 0.13 parts by weight, and 0.43 parts by weight of divinylbenzene (DVB) was used as a cross-linkable monomer, instead of N,N'-methylenebisacrylamide (MBAA), and further that 15 parts by weight of polyvinyl pyrrolidone (PVP) was used as a water-soluble polymer.

Comparative Example 7

A sheet-like hydrogel was obtained in the same manner as that of the above-described Comparative Example 6, with the exception that 0.43 parts by weight of N,N-methylenebisacrylamide (MBAA) was used as a crosslinkable monomer, instead of divinylbenzene (DVB).

Comparative Example 8

A sheet-like hydrogel was obtained in the same manner as that of the above-described Comparative Example 3, with the exceptions that the mixed amount of acrylamide (AAM) was changed to 18 parts by weight, that the mixed amount of N,N'-methylenebisacrylamide (MBAA) was changed to 0.036 parts by weight, the mixed amount of glycerin was changed to 57.474 parts by weight, that the mixed amount of ion exchange water was changed to 22.36 parts by weight, that the mixed amount of the photopolymerization initiator was changed to 0.13 parts by weight, and further that diacetone acrylamide (DAAM) was not used.

(Evaluation of Hydrogel)

With regard to the hydrogel obtained in each of Examples 1 to 22 and Comparative Examples 1 to 8, the swelling rate and the adhesiveness retention rate were measured, after the hydrogel had been exposed to a high humidity environment. In addition, the plasticizer loss ratio was measured, after the hydrogel had been immersed in ion exchange water. Hereafter, methods of measuring individual characteristic values are described.

(Method of Measuring Swelling Rate)

The hydrogel (gel sheet) with a thickness of 0.75 mm obtained in each of Examples 1 to 22 and Comparative Examples 1 to 8 was cut into a size of 20 mm wide×120 mm long, and a PET film (top film) was then peeled from one surface thereof. This surface was lined with a synthetic paper with a thickness of 80 μm (e.g., "Peach Coated Paper SE80" manufactured by Nisshinbo Paper Products Corp., or "FGS80" manufactured by Yupo Corporation) to produce a test piece. After a PET film (base film) had been peeled from the other surface of the hydrogel in this test piece, the weight of the hydrogel was then measured. The obtained weight was defined as a weight before exposure to a high humidity environment. Thereafter, the test piece was left at rest in a constant temperature bath at 40° C. at a relative humidity of 90% for 1 hour. After 1 hour had passed, the weight of the hydrogel was measured. Then, the swelling rate was calculated according to the following equations.

Swelling rate (%)=$W1/W0 \times 100$ $W0$=Weight (g) of hydrogel before being exposed to high humidity environment $W1$=Weight (g) of hydrogel after being exposed to high humidity environment (Method of Measuring Adhesiveness Retention Rate)

The hydrogel (gel sheet) with a thickness of 0.75 mm obtained in each of Examples 1 to 22 and Comparative Examples 1 to 8 was cut into a size of 20 mm wide×120 mm long, and a PET film (top film) was then peeled from one surface thereof. This surface was lined with a synthetic paper with a thickness of 80 μm (e.g., "Peach Coated Paper SE80" manufactured by Nisshinbo Paper Products Corp., or "FGS80" manufactured by Yupo Corporation) to produce a test piece. The surface of this test piece, from which a PET film (base film) had been peeled, was attached to a Bakelite plate, and was then equipped into Tensilon ("RTE-1210" manufactured by ORIENTIC Co., Ltd.). Thereafter, a load was measured, when the test piece was peeled in the direction of 90° at a rate of 300 mm/min in the environment of 23° C. and a relative humidity of 55% in accordance with JIS Z 0237. The measured load (gf/20 mm) was defined as an initial adhesive force. In addition, the hydrogel was left at rest in a constant temperature bath at 40° C. at a relative humidity of 90%, in a state in which the PET film was peeled from the above-described test piece, and thereafter, the hydrogel was attached to a Bakelite plate in the same manner as described above. After that, a load was measured, when the test piece was peeled in the direction of 90° at a rate of 300 mm/min in the environment of 23° C. and a relative humidity of 55% in accordance with JIS Z 0237. The measured load (gf/20 mm) was defined as an adhesive force after exposure to a high humidity environment. The adhesiveness retention rate was calculated according to the following equations.

Adhesiveness retention rate (%)=$F1/F0\times100$

F0=Initial adhesive force of hydrogel
F1=Adhesive force of hydrogel after being exposed to high humidity environment
(Method of Measuring Plasticizer Loss Ratio)
A hydrogel, which had been cut into a size of 40 mm square and had previously been measured in terms of weight (g), was dried in an oven at 120° C. for 120 minutes. Thereafter, the weight (g) thereof was measured, and the loss rate of water existing in the hydrogel was calculated according to the following equation (G0). On the other hand, the gel, which had previously been measured in terms of weight (g), was immersed in ion exchange water at 20° C. for 60 minutes, and was then dried in an oven at 120° C. for 240 minutes. Thereafter, the weight (g) thereof was measured, and the loss rate of water existing in the hydrogel was calculated according to the following equation (G1). Furthermore, the plasticizer loss ratio was calculated according to the following equation.

Plasticizer loss ratio=$G1/G0$

Water loss rate $(G0)(\%)$=(Weight of gel−weight of gel after drying)/weight of gel×100

Water loss rate $(G1)(\%)$=(Weight of gel−weight of gel after water immersion and drying)/weight of gel×100

The composition of the hydrogel in each of Examples 1 to 22 and Comparative Examples 1 to 8, and the swelling rate, plasticizer loss ratio, and adhesiveness retention rate of each hydrogel are summarized in the following table.

TABLE 1

| | | | | | Example | | | |
|---|---|---|---|---|---|---|---|---|
| | | | | | 1 | 2 | 3 | 4 |
| Composition of mixed solution (% by weight) | Monofunctional monomer | | | AAM | 15 | 15 | 15 | 15 |
| | | | | DAAM | 15 | 15 | 15 | 15 |
| | | | | 4HBA | — | — | — | — |
| | | | | AA | — | — | — | — |
| | | | | DMAA | — | — | — | — |
| | | | | DEAA | — | — | — | — |
| | | | | ACMO | — | — | — | — |
| | | | | AME-400 | — | — | — | — |
| | | | | TBAS | — | — | — | — |
| | Crosslinkable monomer | | | MBAA | 0.06 | 0.06 | 0.06 | 0.06 |
| | | | | DVB | — | — | — | — |
| | Plasticizer | Polyoxyalkylene alkyl ether | Multi-chain type | MG-20E | 42.79 | — | — | — |
| | | | | MG-10E | — | 42.79 | — | — |
| | | | | MG-10P | — | — | — | — |
| | | | Straight-chain type | Nonion K-230 | — | — | 42.79 | — |
| | | Sugar | Disaccharide | Sucrose | — | — | — | 21.12 |
| | | Polyhydric alcohol | Sugar alcohol | Sorbitol | — | — | — | — |
| | | | Alcohol | Glycerin | — | — | — | — |
| | | | | PEG | — | — | — | — |
| | Water-soluble polymer | | | PVP | — | — | — | — |
| | pH adjustment | | | 48% sodium hydroxide aqueous solution | | | | |
| | Water | | | Ion exchange water | 25 | 25 | 25 | 46.67 |
| | Electrolyte | | | Sodium chloride | 2 | 2 | 2 | 2 |
| | Photopolymerization initiator | | | Igracure2959 | 0.15 | 0.15 | 0.15 | 0.15 |
| Evaluation item | Total amount | | | | 100 | 100 | 100 | 100 |
| | Swelling rate (%) | | | | 112 | 110 | 109 | 100 |
| | | | | Judgement | ○ | ○ | ○ | ○ |
| | Plasticizer loss ratio | | | | 1.89 | 1.79 | 1.24 | 1.44 |
| | | | | Judgement | ○ | ○ | ○ | ○ |
| | Adhesive force (gf/20 mm) | | Initial stage | | 487 | 453 | 474 | 100 |
| | | | | Judgement | ○ | ○ | ○ | ○ |
| | | | After exposure to high humidity environment | | 404 | 378 | 395 | 220 |
| | Adhesiveness retention rate (%) | | | | 83 | 83 | 83 | 220 |
| | | | | Judgement | ○ | ○ | ○ | ○ |

TABLE 1-continued

|  |  |  |  |  | Example | | | |
|---|---|---|---|---|---|---|---|---|
|  |  |  |  |  | 5 | 6 | 7 | 8 |
| Composition of mixed solution (% by weight) | Monofunctional monomer |  |  | AAM | 15 | 12.5 | 14 | 17.5 |
|  |  |  |  | DAAM | — | 12.5 | 14 | 17.5 |
|  |  |  |  | 4HBA | 15 | — | — | — |
|  |  |  |  | AA | — | — | — | — |
|  |  |  |  | DMAA | — | — | — | — |
|  |  |  |  | DEAA | — | — | — | — |
|  |  |  |  | ACMO | — | — | — | — |
|  |  |  |  | AME-400 | — | — | — | — |
|  |  |  |  | TBAS | — | — | — | — |
|  | Crosslinkable monomer |  |  | MBAA | 0.06 | 0.05 | 0.056 | 0.07 |
|  |  |  |  | DVB | — | — | — | — |
|  | Plasticizer | Polyoxyalkylene alkyl ether | Multi-chain type | MG-20E | 42.79 | 47.8 | 44.794 | 37.78 |
|  |  |  |  | MG-10E | — | — | — | — |
|  |  |  |  | MG-10P | — | — | — | — |
|  |  |  | Straight-chain type | Nonion K-230 | — | — | — | — |
|  |  | Sugar | Disaccharide | Sucrose | — | — | — | — |
|  |  | Polyhydric alcohol | Sugar alcohol | Sorbitol | — | — | — | — |
|  |  |  | Alcohol | Glycerin | — | — | — | — |
|  |  |  |  | PEG | — | — | — | — |
|  | Water-soluble polymer |  |  | PVP | — | — | — | — |
|  | pH adjustment |  |  | 48% sodium hydroxide aqueous solution | — | — | — | — |
|  | Water |  |  | Ion exchange water | 25 | 25 | 25 | 25 |
|  | Electrolyte |  |  | Sodium chloride | 2 | 2 | 2 | 2 |
|  | Photopolymerization initiator |  |  | Igracure2959 | 0.15 | 0.15 | 0.15 | 0.15 |
|  | Total amount |  |  |  | 100 | 100 | 100 | 100 |
| Evaluation item | Swelling rate (%) |  |  |  | 110 | 111 | 110 | 110 |
|  |  |  |  | Judgement | ○ | ○ | ○ | ○ |
|  | Plasticizer loss ratio |  |  |  | 1.41 | 1.94 | 1.91 | 1.70 |
|  |  |  |  | Judgement | ○ | ○ | ○ | ○ |
|  | Adhesive force (gf/20 mm) | Initial stage |  |  | 343 | 830 | 564 | 613 |
|  |  |  |  | Judgement | ○ | ○ | ○ | ○ |
|  |  | After exposure to high humidity environment |  |  | 323 | 512 | 479 | 473 |
|  | Adhesiveness retention rate (%) |  |  |  | 94 | 62 | 85 | 77 |
|  |  |  |  | Judgement | ○ | ○ | ○ | ○ |

|  |  |  |  |  | Example | | | |
|---|---|---|---|---|---|---|---|---|
|  |  |  |  |  | 9 | 10 | 11 | 12 |
| Composition of mixed solution (% by weight) | Monofunctional monomer |  |  | AAM | 20 | 15 | 15 | 15 |
|  |  |  |  | DAAM | 20 | 15 | 15 | 15 |
|  |  |  |  | 4HBA | — | — | — | — |
|  |  |  |  | AA | — | — | — | — |
|  |  |  |  | DMAA | — | — | — | — |
|  |  |  |  | DEAA | — | — | — | — |
|  |  |  |  | ACMO | — | — | — | — |
|  |  |  |  | AME-400 | — | — | — | — |
|  |  |  |  | TBAS | — | — | — | — |
|  | Crosslinkable monomer |  |  | MBAA | 0.08 | 0.06 | 0.06 | 0.06 |
|  |  |  |  | DVB | — | — | — | — |
|  | Plasticizer | Polyoxyalkylene alkyl ether | Multi-chain type | MG-20E | 32.77 | 21.12 | 47.45 | 54.23 |
|  |  |  |  | MG-10E | — | — | — | — |
|  |  |  |  | MG-10P | — | — | — | — |
|  |  |  | Straight-chain type | Nonion K-230 | — | — | — | — |
|  |  | Sugar | Disaccharide | Sucrose | — | — | — | — |
|  |  | Polyhydric alcohol | Sugar alcohol | Sorbitol | — | — | — | — |
|  |  |  | Alcohol | Glycerin | — | — | — | — |
|  |  |  |  | PEG | — | — | — | — |
|  | Water-soluble polymer |  |  | PVP | — | — | — | — |
|  | pH adjustment |  |  | 48% sodium | — | — | — | — |

TABLE 1-continued

|  |  |  |  |  |  |  |  |
|---|---|---|---|---|---|---|---|
|  |  |  |  | hydroxide aqueous solution |  |  |  |
|  | Water |  | Ion exchange water | 25 | 46.67 | 20.34 | 13.56 |
|  | Electrolyte |  | Sodium chloride | 2 | 2 | 2 | 2 |
|  | Photopolymerization initiator |  | Irgacure2959 | 0.15 | 0.15 | 0.15 | 0.15 |
| Evaluation item | Total amount |  |  | 100 | 100 | 100 | 100 |
|  | Swelling rate (%) |  |  | 109 | 96 | 112 | 114 |
|  |  |  | Judgement | ○ | ○ | ○ | ○ |
|  | Plasticizer loss ratio |  |  | 1.54 | 1.25 | 1.85 | 1.64 |
|  |  |  | Judgement | ○ | ○ | ○ | ○ |
|  | Adhesive force (gf/20 mm) | Initial stage |  | 627 | 208 | 647 | 614 |
|  |  |  | Judgement | ○ | ○ | ○ | ○ |
|  |  | After exposure to high humidity environment |  | 460 | 237 | 463 | 390 |
|  | Adhesiveness retention rate (%) |  |  | 73 | 114 | 72 | 64 |
|  |  |  | Judgement | ○ | ○ | ○ | ○ |

|  |  |  |  |  | Example |  |  |
|---|---|---|---|---|---|---|---|
|  |  |  |  |  | 13 | 14 | 15 |
| Composition of mixed solution (% by weight) | Monofunctional monomer |  |  | AAM | 15 | 15 | 15 |
|  |  |  |  | DAAM | 15 | 15 | 15 |
|  |  |  |  | 4HBA | — | — | — |
|  |  |  |  | AA | — | — | — |
|  |  |  |  | DMAA | — | — | — |
|  |  |  |  | DEAA | — | — | — |
|  |  |  |  | ACMO | — | — | — |
|  |  |  |  | AME-400 | — | — | — |
|  |  |  |  | TBAS | — | — | — |
|  | Crosslinkable monomer |  |  | MBAA | 0.03 | 0.09 | 0.2 |
|  |  |  |  | DVB | — | — | — |
|  | Plasticizer | Polyoxyalkylene alkyl ether | Multi-chain type | MG-20E | 42.82 | 42.76 | 42.65 |
|  |  |  |  | MG-10E | — | — | — |
|  |  |  |  | MG-10P | — | — | — |
|  |  |  | Straight-chain type | Nonion K-230 | — | — | — |
|  |  | Sugar | Disaccharide | Sucrose | — | — | — |
|  |  | Polyhydric alcohol | Sugar alcohol | Sorbitol | — | — | — |
|  |  |  | Alcohol | Glycerin | — | — | — |
|  |  |  |  | PEG | — | — | — |
|  | Water-soluble polymer |  |  | PVP | — | — | — |
|  | pH adjustment |  |  | 48% sodium hydroxide aqueous solution |  |  |  |
|  | Water |  |  | Ion exchange water | 25 | 25 | 25 |
|  | Electrolyte |  |  | Sodium chloride | 2 | 2 | 2 |
|  | Photopolymerization initiator |  |  | Irgacure2959 | 0.15 | 0.15 | 0.15 |
| Evaluation item | Total amount |  |  |  | 100 | 100 | 100 |
|  | Swelling rate (%) |  |  |  | 110 | 109 | 109 |
|  |  |  |  | Judgement | ○ | ○ | ○ |
|  | Plasticizer loss ratio |  |  |  | 1.32 | 1.67 | 1.59 |
|  |  |  |  | Judgement | ○ | ○ | ○ |
|  | Adhesive force (gf/20 mm) | Initial stage |  |  | 1207 | 415 | 222 |
|  |  |  |  | Judgement | ○ | ○ | ○ |
|  |  | After exposure to high humidity environment |  |  | 1012 | 314 | 149 |
|  | Adhesiveness retention rate (%) |  |  |  | 84 | 76 | 67 |
|  |  |  |  | Judgement | ○ | ○ | ○ |

TABLE 1-continued

|  |  |  |  |  | Example |  |  |  |
|---|---|---|---|---|---|---|---|---|
|  |  |  |  |  | 16 | 17 | 18 | 19 |
| Composition of mixed solution (% by weight) | Monofunctional monomer |  |  | AAM | 15 | 15 | 15 | 15 |
|  |  |  |  | DAAM | — | — | — | — |
|  |  |  |  | 4HBA | — | — | — | — |
|  |  |  |  | AA | 15 | — | — | — |
|  |  |  |  | DMAA | — | 15 | — | — |
|  |  |  |  | DEAA | — | — | 15 | — |
|  |  |  |  | ACMO | — | — | — | 15 |
|  |  |  |  | AME-400 | — | — | — | — |
|  |  |  |  | TBAS | — | — | — | — |
|  | Crosslinkable monomer |  |  | MBAA | 0.06 | 0.06 | 0.06 | 0.06 |
|  |  |  |  | DVB | — | — | — | — |
|  | Plasticizer | Polyoxyalkylene alkyl ether | Multi-chain type | MG-20E | 42.79 | 42.79 | 42.79 | 33.895 |
|  |  |  |  | MG-10E | — | — | — | — |
|  |  |  |  | MG-10P | — | — | — | — |
|  |  |  | Straight-chain type | Nonion K-230 | — | — | — | — |
|  |  | Sugar | Disaccharide | Sucrose | — | — | — | — |
|  |  | Polyhydric alcohol | Sugar alcohol | Sorbitol | — | — | — | — |
|  |  |  | Alcohol | Glycerin | — | — | — | — |
|  |  |  |  | PEG | — | — | — | — |
|  | Water-soluble polymer |  |  | PVP | — | — | — | — |
|  | pH adjustment |  |  | 48% sodium hydroxide aqueous solution | — | — | — | — |
|  | Water |  |  | Ion exchange water | 25 | 25 | 25 | 33.895 |
|  | Electrolyte |  |  | Sodium chloride | 2 | 2 | 2 | 2 |
|  | Photopolymerization initiator |  |  | Irgacure2959 | 0.15 | 0.15 | 0.15 | 0.15 |
| Evaluation item | Total amount |  |  |  | 100 | 100 | 100 | 100 |
|  | Swelling rate (%) |  |  |  | 110 | 113 | 113 | 107 |
|  |  |  |  | Judgement | ○ | ○ | ○ | ○ |
|  | Plasticizer loss ratio |  |  |  | 1.59 | 0.86 | 1.66 | 1.43 |
|  |  |  |  | Judgement | ○ | ○ | ○ | ○ |
|  | Adhesive force (gf/20 mm) | Initial stage |  |  | 679 | 400 | 1168 | 116 |
|  |  |  |  | Judgement | ○ | ○ | ○ | ○ |
|  |  | After exposure to high humidity environment |  |  | 415 | 265 | 805 | 113 |
|  | Adhesiveness retention rate (%) |  |  |  | 61 | 66 | 69 | 68 |
|  |  |  |  | Judgement | ○ | ○ | ○ | ○ |

|  |  |  |  |  | Example |  |  |
|---|---|---|---|---|---|---|---|
|  |  |  |  |  | 20 | 21 | 22 |
| Composition of mixed solution (% by weight) | Monofunctional monomer |  |  | AAM | 15 | — | — |
|  |  |  |  | DAAM | — | 15 | — |
|  |  |  |  | 4HBA | — | — | — |
|  |  |  |  | AA | — | — | 15 |
|  |  |  |  | DMAA | — | — | — |
|  |  |  |  | DEAA | — | — | — |
|  |  |  |  | ACMO | — | — | — |
|  |  |  |  | AME-400 | 15 | — | — |
|  |  |  |  | TBAS | — | 15 | 15 |
|  | Crosslinkable monomer |  |  | MBAA | 0.06 | 0.06 | 0.06 |
|  |  |  |  | DVB | — | — | — |
|  | Plasticizer | Polyoxyalkylene alkyl ether | Multi-chain type | MG-20E | 42.79 | 39.99 | 29.52 |
|  |  |  |  | MG-10E | — | — | — |
|  |  |  |  | MG-10P | — | — | — |
|  |  |  | Straight-chain type | Nonion K-230 | — | — | — |
|  |  | Sugar | Disaccharide | Sucrose | — | — | — |
|  |  | Polyhydric alcohol | Sugar alcohol | Sorbitol | — | — | — |
|  |  |  | Alcohol | Glycerin | — | — | — |
|  |  |  |  | PEG | — | — | — |
|  | Water-soluble polymer |  |  | PVP | — | — | — |
|  | pH adjustment |  |  | 48% sodium | — | 5.84 | 9.10 |

TABLE 1-continued

|  |  |  |  |  |  |  |
|---|---|---|---|---|---|---|
|  |  |  | hydroxide aqueous solution |  |  |  |
|  | Water |  | Ion exchange water | 25 | 21.96 | 29.17 |
|  | Electrolyte |  | Sodium chloride | 2 | 2 | 2 |
|  | Photopolymerization initiator |  | Irgacure2959 | 0.15 | 0.15 | 0.15 |
| Evaluation item | Total amount |  |  | 100 | 100 | 100 |
|  | Swelling rate (%) |  |  | 113 | 113 | 112 |
|  |  |  | Judgement | ○ | ○ | ○ |
|  | Plasticizer loss ratio |  |  | 1.65 | 0.84 | 1.24 |
|  |  |  | Judgement | ○ | ○ | ○ |
|  | Adhesive force (gf/20 mm) | Initial stage |  | 344 | 509 | 205 |
|  |  |  | Judgement | ○ | ○ | ○ |
|  |  | After exposure to high humidity environment |  | 235 | 310 | 124 |
|  | Adhesiveness retention rate (%) |  |  | 68 | 61 | 61 |
|  |  |  | Judgement | ○ | ○ | ○ |

|  |  |  |  | Comparative Example |  |  |  |  |
|---|---|---|---|---|---|---|---|---|
|  |  |  |  | 1 | 2 | 3 | 4 | 5 |
| Composition of mixed solution (% by weight) | Monofunctional monomer |  | AAM | 15 | 15 | 15 | 15 | 15 |
|  |  |  | DAAM | 15 | 15 | 15 | 15 | 15 |
|  |  |  | 4HBA | — | — | — | — | — |
|  |  |  | AA | — | — | — | — | — |
|  |  |  | DMAA | — | — | — | — | — |
|  |  |  | DEAA | — | — | — | — | — |
|  |  |  | ACMO | — | — | — | — | — |
|  |  |  | AME-400 | — | — | — | — | — |
|  |  |  | TBAS | — | — | — | — | — |
|  | Crosslinkable monomer |  | MBAA | 0.06 | 0.06 | 0.06 | 0.06 | 0.06 |
|  |  |  | DVB | — | — | — | — | — |
|  | Plasticizer | Polyoxyalkylene alkyl ether | Multi-chain type | MG-20E | — | — | — | — | 61.01 |
|  |  |  | MG-10E | — | — | — | — | — |
|  |  |  | MG-10P | 42.79 | — | — | — | — |
|  |  | Straight-chain type | Nonion K-230 | — | — | — | — | — |
|  |  | Sugar | Disaccharide | Sucrose | — | — | — | — | — |
|  |  | Polyhydric alcohol | Sugar alcohol | Sorbitol | — | 42.79 | — | — | — |
|  |  |  | Alcohol | Glycerin | — | — | 42.79 | — | — |
|  |  |  |  | PEG | — | — | — | 42.79 | — |
|  | Water-soluble polymer |  | PVP | — | — | — | — | — |
|  | pH adjustment |  | 48% sodium hydroxide aqueous solution | — | — | — | — | — |
|  | Water |  | Ion exchange water | 25 | 25 | 25 | 25 | 6.78 |
|  | Electrolyte |  | Sodium chloride | 2 | 2 | 2 | 2 | 2 |
|  | Photopolymerization initiator |  | Irgacure2959 | 0.15 | 0.15 | 0.15 | 0.15 | 0.15 |
| Evaluation item | Total amount |  |  | 100 | 100 | 100 | 100 | 100 |
|  | Swelling rate (%) |  |  | 104 | Non-producible | 121 | 114 | 115 |
|  |  |  | Judgement | ○ |  | x | ○ | ○ |
|  | Plasticizer loss ratio |  |  | 1.24 |  | 2.02 | 2.41 | 1.22 |
|  |  |  | Judgement | ○ |  | x | x | ○ |
|  | Adhesive force (gf/20 mm) | Initial stage |  | 18 |  | 347 | 450 | Non-measurable |
|  |  |  | Judgement | x |  | ○ | ○ |  |
|  |  | After exposure to high humidity environment |  | 17 |  | 94 | 248 |  |
|  | Adhesiveness retention rate (%) |  |  | 93 |  | 27 | 55 |  |
|  |  |  | Judgement | ○ |  | x | x |  |

TABLE 1-continued

|  |  |  |  |  | Comparative Example | | |
|---|---|---|---|---|---|---|---|
|  |  |  |  |  | 6 | 7 | 8 |
| Composition of mixed solution (% by weight) | Monofunctional monomer |  |  | AAM | 10 | 10 | 18 |
|  |  |  |  | DAAM | 15 | 15 | — |
|  |  |  |  | 4HBA | — | — | — |
|  |  |  |  | AA | — | — | — |
|  |  |  |  | DMAA | — | — | — |
|  |  |  |  | DEAA | — | — | — |
|  |  |  |  | ACMO | — | — | — |
|  |  |  |  | AME-400 | — | — | — |
|  |  |  |  | TBAS | — | — | — |
|  | Crosslinkable monomer |  |  | MBAA | — | 0.43 | 0.036 |
|  |  |  |  | DVB | 0.43 | — | — |
|  | Plasticizer | Polyoxyalkylene alkyl ether | Multi-chain type | MG-20E | — | — | — |
|  |  |  |  | MG-10E | — | — | — |
|  |  |  |  | MG-10P | — | — | — |
|  |  |  | Straight-chain type | Nonion K-230 | — | — | — |
|  |  | Sugar | Disaccharide | Sucrose | — | — | — |
|  |  | Polyhydric alcohol | Sugar alcohol | Sorbitol | — | — | — |
|  |  |  | Alcohol | Glycerin | — | — | 57.474 |
|  |  |  |  | PEG | 33.94 | 33.94 | — |
|  | Water-soluble polymer |  |  | PVP | 15 | 15 | — |
|  | pH adjustment |  |  | 48% sodium hydroxide aqueous solution | — | — | — |
|  | Water |  |  | Ion exchange water | 25 | 25 | 22.36 |
|  | Electrolyte |  |  | Sodium chloride | 0.5 | 0.5 | 2 |
|  | Photopolymerization initiator |  |  | Irgacure2959 | 0.13 | 0.13 | 0.13 |
|  | Total amount |  |  |  | 100 | 100 | 100 |
| Evaluation item | Swelling rate (%) |  |  |  | 111 | 112 | 126 |
|  |  |  |  | Judgement | ○ | ○ | x |
|  | Plasticizer loss ratio |  |  |  | 2.22 | 2.06 | 2.45 |
|  |  |  |  | Judgement | x | x | x |
|  | Adhesive force (gf/20 mm) | Initial stage |  |  | 202 | 92 | 397 |
|  |  |  |  | Judgement | ○ | x | ○ |
|  |  | After exposure to high humidity environment |  |  | 119 | 34 | 98 |
|  | Adhesiveness retention rate (%) |  |  |  | 59 | 37 | 25 |
|  |  |  |  | Judgement | x | x | x |

As shown in the above table, the swelling rates of the hydrogels of Examples 1 to 22 were all 115% or less, after the hydrogels had been exposed to the environment of 40° C. and a relative humidity of 90% for 1 hour, and further that the plasticizer loss ratio thereof was less than 2.

Further, the initial adhesive force of the hydrogel in each of Examples 1 to 22 to a Bakelite plate in the environment of 23° C. and a relative humidity of 55% was 100 gf/20 mm or more, and the adhesiveness retention rate after each hydrogel had been exposed to the environment of 40° C. and a relative humidity of 90% for 1 hour was 60% or more. Accordingly, it is found that the hydrogels of Examples 1 to 22 can retain the initial high adhesive force, without a reduction in the adhesive force, even when they are used in a high humidity environment in which sweat and the like adhere to the hydrogels.

In contrast, the hydrogels of Comparative Examples 3, 4 and 6 to 8, into which polyhydric alcohol had been mixed as a plasticizer, had a high plasticizer loss ratio, and the adhesive force thereof was reduced by being exposed to a high humidity environment. Moreover, the hydrogel of Comparative Example 1 had a low initial adhesive force, and thus, it was unsuitable as a hydrogel to be attached to a living body. The hydrogel of Comparative Example 2, into which polyhydric alcohol, sorbitol, had been mixed as a plasticizer, exhibited poor compatibility, and therefore, a hydrogel could not be produced. Furthermore, since the hydrogel of Comparative Example 5 comprised more than 60% by weight of polyoxyethylene methyl glucoside (MG-20E), its gel skeleton became fragile after the hydrogel had been exposed to a high humidity environment, and gel destruction occurred upon the measurement of the adhesiveness. Therefore, the adhesive force thereof could not be measured.

REFERENCE SIGNS LIST

1 Gel sheet
10 Hydrogel
20 Base film
30 Top film
40 Intermediate base material

All publications, patents and patent applications cited in the present description are incorporated herein by reference in their entirety.

The invention claimed is:

1. A hydrogel comprising:
a polymer matrix formed from a copolymer of
- a monofunctional monomer having one ethylenically unsaturated group, the monofunctional monomer comprising acrylamide and diacetoneacrylamide, the monofunctional monomer being present at 25-40% by weight with respect to 100% by weight of the hydrogel and
- a crosslinkable monomer, the crosslinkable monomer comprised of N,N'-methylenebisacrylamide and being present at 0.03 to 0.2% by weight with respect to 100% by weight of the hydrogel, water, and
a plasticizer consisting of polyoxyethylene methyl glucoside having 10 to 20 oxyethylene units,
in which the plasticizer is present at 21.12% to 54.23% by weight, with respect to 100% by weight of the hydrogel, wherein:
- the plasticizer loss ratio is less than 2,
- the swelling rate is 115% or less when the hydrogel is exposed to the environment of 40° C. and 90% RH for 1 hour, and
- the initial adhesive force to a Bakelite plate is 100 gf/20 mm or more in an environment of 23° C. and 55% RH.

2. The hydrogel according to claim 1, wherein the adhesive force obtained after the hydrogel is exposed to the environment of 40° C. and 90% RH for 1 hour is 60% or more, with respect to the initial adhesive force.

3. The hydrogel according to claim 1, which is used as a medical electrode in monitoring devices or devices for performing treatments using electrical stimulation, an indifferent plate of a cautery knife, an adhesive tape, or a wound covering material.

* * * * *